(12) United States Patent
Feldman et al.

(10) Patent No.: US 9,535,027 B2
(45) Date of Patent: Jan. 3, 2017

(54) ANALYTE SENSORS AND METHODS OF USING SAME

(71) Applicant: Abbott Diabetes Care Inc., Alameda, CA (US)

(72) Inventors: Benjamin J. Feldman, Oakland, CA (US); Zenghe Liu, Alameda, CA (US); Tianmei Ouyang, Fremont, CA (US); Suyue Qian, Fremont, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 570 days.

(21) Appl. No.: 13/949,996

(22) Filed: Jul. 24, 2013

(65) Prior Publication Data

US 2014/0026646 A1 Jan. 30, 2014

Related U.S. Application Data

(60) Provisional application No. 61/675,696, filed on Jul. 25, 2012.

(51) Int. Cl.
*G01N 27/327* (2006.01)

(52) U.S. Cl.
CPC ........ *G01N 27/327* (2013.01); *G01N 27/3272* (2013.01)

(58) Field of Classification Search
CPC .............. G01N 27/3272; G01N 27/327; G01N 27/3273; G01N 27/3271; G01N 27/307; G01N 27/3275; G01N 27/30; G01N 27/301
USPC ....................................................... 73/61.43
See application file for complete search history.

(56) References Cited

U.S. PATENT DOCUMENTS

| | | | |
|---|---|---|---|
| 5,262,035 A | 11/1993 | Gregg et al. | |
| 5,264,104 A | 11/1993 | Gregg et al. | |
| 5,320,725 A | 6/1994 | Gregg et al. | |
| 5,356,786 A | 10/1994 | Heller et al. | |
| 6,143,164 A | 11/2000 | Heller et al. | |
| 6,281,006 B1 | 8/2001 | Heller et al. | |
| 6,592,745 B1 | 7/2003 | Feldman et al. | |
| 6,616,819 B1 | 9/2003 | Liamos et al. | |
| 6,627,057 B1 * | 9/2003 | Bhullar ............... | G01N 27/3272 204/403.01 |
| 6,638,716 B2 | 10/2003 | Heller et al. | |
| 6,676,815 B1 * | 1/2004 | Bhullar ............... | G01N 27/3272 204/403.01 |
| 6,736,957 B1 | 5/2004 | Forrow et al. | |
| 6,932,894 B2 | 8/2005 | Mao et al. | |
| 7,501,053 B2 | 3/2009 | Karinka et al. | |
| 7,866,026 B1 | 1/2011 | Wang et al. | |

(Continued)

OTHER PUBLICATIONS

Clarke et al., "Evaluating Clinical Accuracy of Systems for Self-Monitoring of Blood Glucose," *Diabetes Care* 10(5):622-628 (1987).

*Primary Examiner* — Marrit Eyassu
(74) *Attorney, Agent, or Firm* — Edward J. Baba; Shweta Chandra; Bozicevic, Field & Francis LLP

(57) ABSTRACT

Provided are sensors for determining the concentration of an analyte in a sample fluid. In certain embodiments, the sensors include conductive particles and exhibit improved uniformity of distribution of one or more sensing chemistry components, increased effective working electrode surface area, and/or reduced entry of interfering components into a sample chamber of the sensor. Methods of using and manufacturing the sensors are also provided.

28 Claims, 6 Drawing Sheets

(56) References Cited

U.S. PATENT DOCUMENTS

| | | |
|---|---|---|
| 8,262,874 B2 | 9/2012 | Forrow et al. |
| 2006/0025662 A1 | 2/2006 | Buse et al. |
| 2006/0091006 A1 | 5/2006 | Wang et al. |
| 2007/0068807 A1 | 3/2007 | Feldman et al. |
| 2007/0095661 A1 | 5/2007 | Wang et al. |
| 2007/0108048 A1 | 5/2007 | Wang et al. |
| 2007/0199818 A1 | 8/2007 | Petyt et al. |
| 2007/0246357 A1* | 10/2007 | Wu ............... C12Q 1/005 204/403.01 |
| 2008/0060196 A1* | 3/2008 | Wang ............. G01N 27/3272 29/854 |
| 2008/0066305 A1 | 3/2008 | Wang et al. |
| 2008/0102441 A1 | 5/2008 | Chen et al. |
| 2008/0148873 A1 | 6/2008 | Wang |
| 2008/0156662 A1* | 7/2008 | Wu ............... C12Q 1/004 205/787 |
| 2008/0179187 A1 | 7/2008 | Ouyang et al. |
| 2008/0267823 A1 | 10/2008 | Wang et al. |
| 2009/0029479 A1* | 1/2009 | Docherty ........ C12Q 1/004 436/149 |
| 2009/0038939 A1* | 2/2009 | Popovich ....... G01N 27/3272 204/401 |
| 2009/0057146 A1* | 3/2009 | Teodorczyk .... C12Q 1/001 204/403.01 |
| 2009/0095625 A1 | 4/2009 | Forrow |
| 2010/0243476 A1* | 9/2010 | Fujiwara ........ G01N 27/3274 205/777.5 |
| 2012/0088993 A1* | 4/2012 | Buck ............. A61B 5/1473 600/345 |

\* cited by examiner

FIG. 1
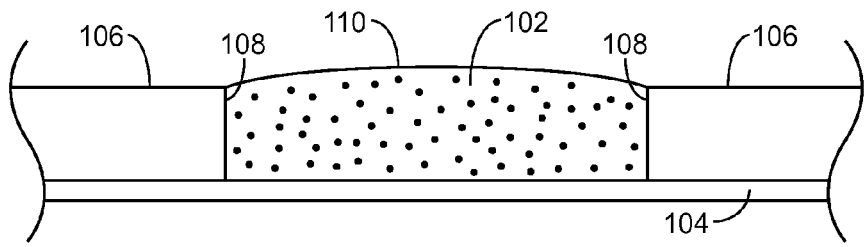
FIG. 1A
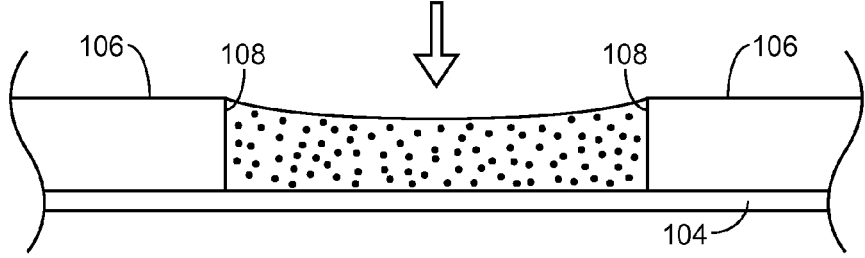
FIG. 1B
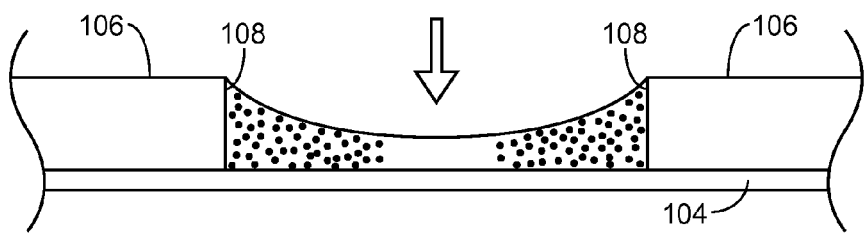
FIG. 1C
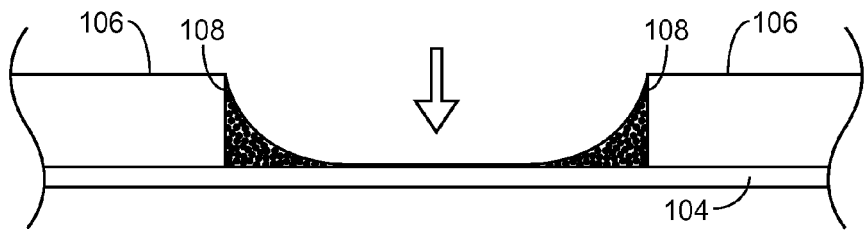
FIG. 1D
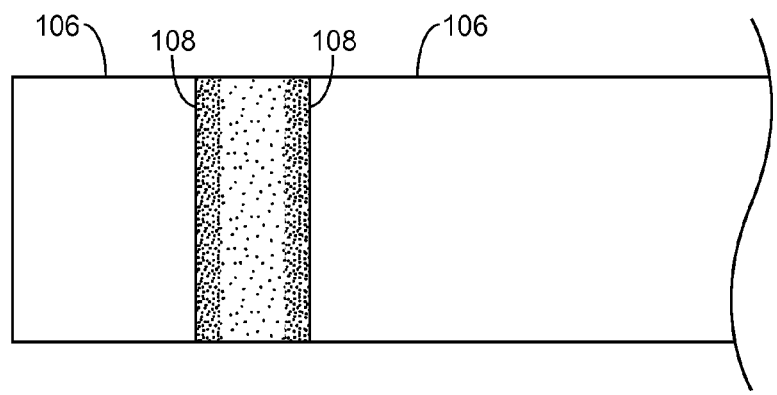
FIG. 1E

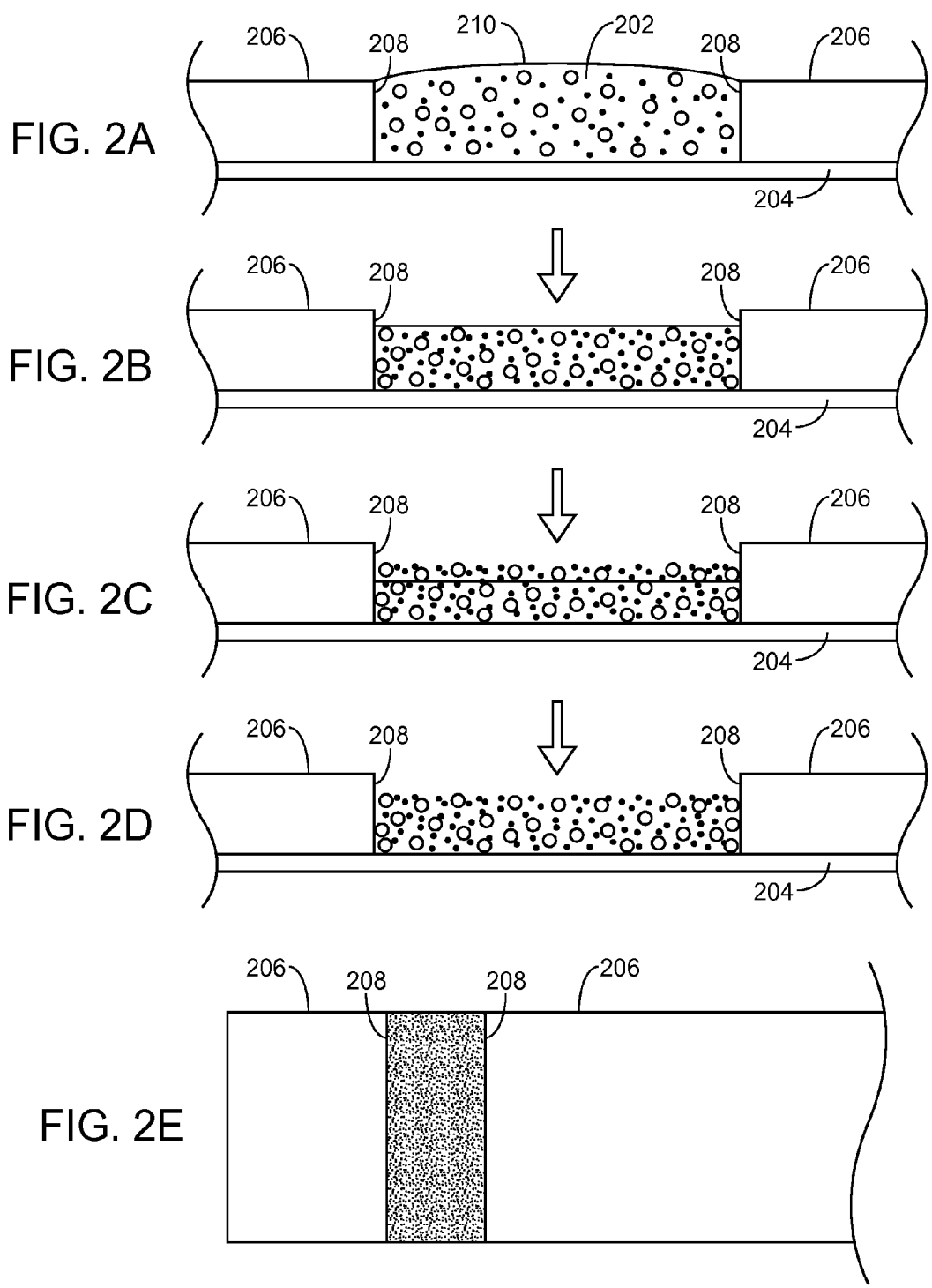

FIG. 6
FIG. 6A
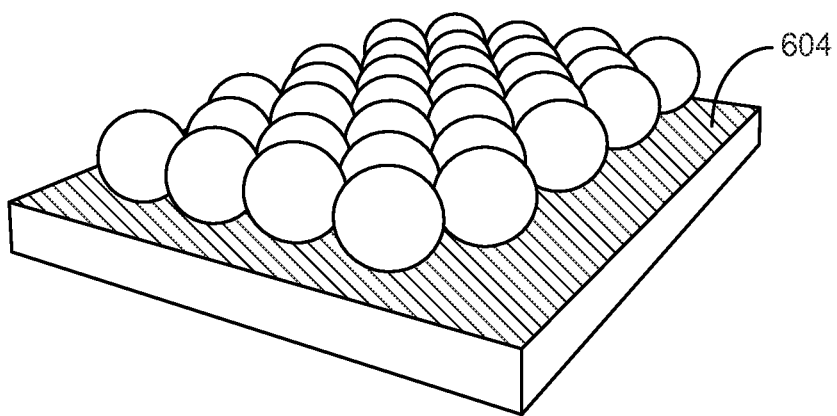
FIG. 6B
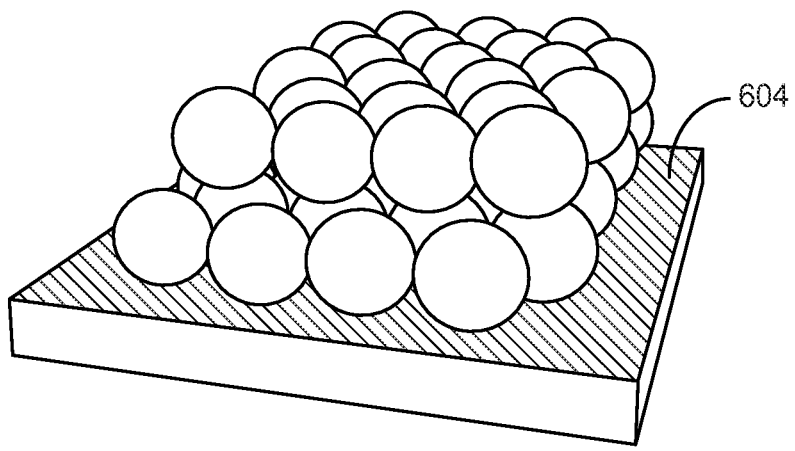

ANALYTE SENSORS AND METHODS OF USING SAME

CROSS-REFERENCE TO RELATED APPLICATIONS

This application claims priority based on U.S. Provisional Application No. 61/675,696, filed Jul. 25, 2012, the disclosure of which is incorporated by reference herein in its entirety.

INTRODUCTION

In many instances it is desirable or necessary to regularly monitor the concentration of particular constituents in a fluid. A number of systems are available that analyze the constituents of bodily fluids such as blood, urine and saliva. Examples of such systems conveniently monitor the level of particular medically significant fluid constituents, such as, for example, cholesterol, ketones, vitamins, proteins, and various metabolites or blood sugars, such as glucose. Diagnosis and management of patients suffering from diabetes mellitus, a disorder of the pancreas where insufficient production of insulin prevents normal regulation of blood sugar levels, requires carefully monitoring of blood glucose levels on a daily basis. A number of systems that allow individuals to easily monitor their blood glucose are currently available. Such systems include electrochemical biosensors, including those that comprise a glucose sensor that is adapted to determine the concentration of an analyte in a bodily fluid (e.g., blood) sample.

A person may obtain a blood sample by withdrawing blood from a blood source in his or her body, such as a vein, using a needle and syringe, for example, or by lancing a portion of his or her skin, using a lancing device, for example, to make blood available external to the skin, to obtain the necessary sample volume for in vitro testing. The person may then apply the fresh blood sample to a test strip, whereupon suitable detection methods, such as colorimetric, electrochemical, or photometric detection methods, for example, may be used to determine the person's actual blood glucose level.

Analyte sensors with improved performance, such as increased accuracy and response times, are desirable. The present disclosure provides sensors, and methods of using such sensors, meeting these and a variety of other needs.

SUMMARY

Provided are sensors for determining the concentration of an analyte in a sample fluid. In certain embodiments, the sensors include conductive particles and exhibit improved uniformity of distribution of one or more sensing chemistry components, increased effective working electrode surface area, and/or reduced entry of interfering components into a sample chamber of the sensor. Methods of using and manufacturing the sensors are also provided.

BRIEF DESCRIPTION OF THE FIGURES

FIGS. 1A-1E show a schematic view of non-uniform reagent distribution upon drying of a detection reagent solution in the sample chamber of a sensor.

FIGS. 2A-2E show a schematic view of substantially uniform reagent distribution upon drying of a particle-containing detection reagent solution in the sample chamber of a sensor.

FIGS. 6A and 6B are microscopic images depicting an approximate monolayer of conductive particles disposed on a working electrode surface.

DETAILED DESCRIPTION

Figure 3:
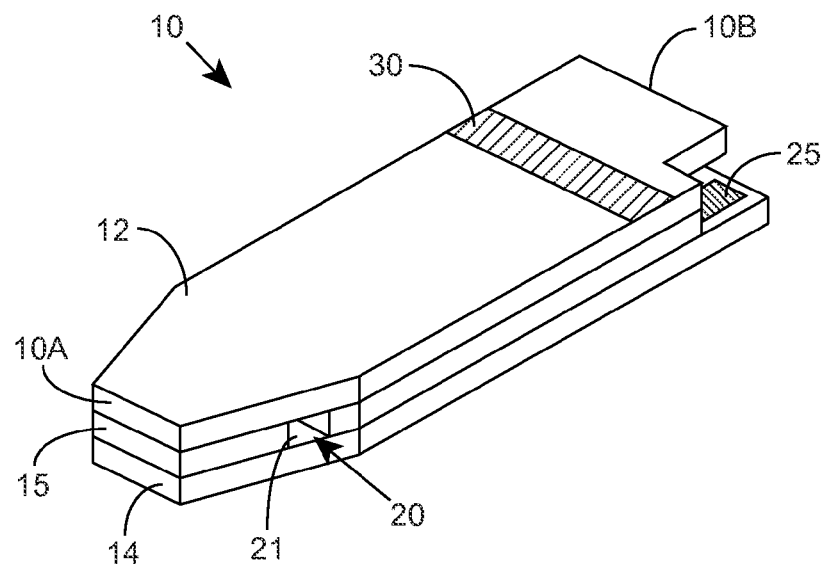
FIG. 3 is a schematic view of a first embodiment of a sensor strip in accordance with the present disclosure.

Provided are sensors for determining the concentration of an analyte in a sample fluid. In certain embodiments, the sensors include conductive particles and exhibit improved uniformity of distribution of one or more sensing chemistry components, increased effective working electrode surface area, and/or reduced entry of interfering components into a sample chamber of the sensor. Methods of using and manufacturing the sensors are also provided.

Before the sensors and methods of the present disclosure are described in greater detail, it is to be understood that the sensors and methods are not limited to particular embodiments described, as such may, of course, vary. It is also to be understood that the terminology used herein is for the purpose of describing particular embodiments only, and is not intended to be limiting, since the scope of the sensors and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the sensors and methods. The upper and lower limits of these smaller ranges may independently be included in the smaller ranges and are also encompassed within the sensors and methods, subject to any specifically excluded limit in the stated range. Where the stated range includes one or both of the limits, ranges excluding either or both of those included limits are also included in the sensors and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods and materials similar or equivalent to those described herein can also be used in the practice or testing of the sensors and methods, representative illustrative sensors, methods and materials are now described.

All publications and patents cited in this specification are herein incorporated by reference as if each individual publication or patent were specifically and individually indicated to be incorporated by reference and are incorporated herein by reference to disclose and describe the sensors, methods and/or materials in connection with which the publications are cited. The citation of any publication is for its disclosure prior to the filing date and should not be construed as an admission that the present sensors and methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the sensors and methods, which are, for clarity, described in the context of separate embodiments, may also be provided in combination in a single embodiment. Conversely, various features of the sensors and methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present sensors and methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present sensors and methods. Any recited method can be carried out in the order of events recited or in any other order which is logically possible.

Sensors

Disclosed herein are sensors for determining the concentration of an analyte in a sample fluid. In certain embodiments, a sensor having particulate matter disposed on an area of a working electrode of the sensor is provided. For example, a sensor may have conductive particles disposed on all or a portion of a working electrode within a sample chamber of the sensor. In certain aspects, the particulate matter is provided on the surface of a working electrode as part of a composition that includes at least one analyte detection reagent (e.g., an analyte-responsive enzyme and/or a redox mediator) that facilitate detection of an analyte. That is, a composition (e.g., a suspension) that includes, e.g., conductive particles, an analyte-responsive enzyme and/or a redox mediator, may be disposed on all or a portion of a working electrode surface of the sensor. In other embodiments, the particulate matter may first be disposed on a surface of a working electrode, and a composition that includes one or more detection reagents, e.g., an analyte-responsive enzyme and/or a redox mediator, is subsequently disposed on the conductive particles.

In each of the sensor embodiments of the present disclosure, the conductive particles may be configured and arranged to provide for more even distribution of the sensing reagents on the surface of the working electrode as compared to the distribution absent the particles, increase the effective surface area of the working electrode, and/or prevent the entry of interfering substances (e.g., red blood cells) into a sample chamber of the sensor.

Sensors Having Improved Uniformity of Distribution of One or More Analyte Detection Reagents Embodiments of the present disclosure relate to sensors having improved uniformity of distribution of one or more analyte detection reagents by inclusion of particulate matter (e.g., microparticles), where the detection reagent and particulate matter are disposed on a surface of a working electrode of the sensor, such as in vitro or in vivo analyte sensors. For example, embodiments of the present disclosure provide for inclusion of microparticles in a solution, such as a detection reagent solution, resulting in more uniform distribution of the detecting reagent after the detection reagent solution is dried on the surface of the working electrode. Also provided are methods of manufacturing the analyte sensors and methods of using the analyte sensors in analyte monitoring.

In certain aspects, during the manufacturing process for the subject analyte sensors, a detection reagent solution is contacted with a surface of a substrate (e.g., a surface of a working electrode), forming a deposition of the solution on the surface of the substrate. In some cases, the solution is allowed to dry and cure. One difficulty with producing analyte sensors in which the reagent solution is deposited in a channel (e.g., a channel constituting a sample chamber region defined by a spacer layer of the sensor) is that—as the reagent solution dries—the reagent tends to deposit preferentially at the sides of the channel. In such instances, the reagent will not be uniformly distributed across the channel (e.g., along the axis perpendicular to the flow of a sample into the sample chamber), and the center of the channel may be partially denuded of reagent, resulting in the analyte not reacting completely in the center of the channel, particularly at high analyte concentrations (e.g., high blood glucose concentrations). This non-uniformity may adversely affect performance characteristics of the sensor, such as decreasing response times and/or accuracy as compared to a sensor having substantially uniform distribution of the detection reagent on the working electrode surface.

The process of non-uniform reagent distribution as a reagent solution dries in a sample chamber of a sensor is schematically illustrated in FIG. 1. A portion of the partially assembled sensor includes sample chamber 102 defined by substrate 104 and spacer layer 106. As shown in FIGS. 1A-1D, as reagent solution 110 dries, the reagent (shown as dots in reagent solution 110) preferentially deposits at sides 108 of the sample chamber. FIG. 1E shows a top view of the portion of the sensor shown in FIG. 1D.

Embodiments of the present disclosure are based on the discovery that the addition of particulate matter (e.g., carbon nanopowder, microparticles (e.g., conductive microspheres), and/or the like) to a reagent solution used in the manufacture of in vitro or in vivo analyte sensors improves uniformity and/or distribution of one or more detection reagents (e.g., an analyte-responsive enzyme and/or redox mediator) on a surface of the sensor. The principle of adding particulate matter to a reagent solution for improved reagent uniformity and distribution is schematically illustrated in FIG. 2. As shown, a portion of a partially manufactured sensor includes sample chamber 202 defined by substrate 204 (which may be a working electrode surface) and spacer layer 206. Reagent solution 210 is disposed in sample chamber 202 and includes detection reagent(s) (shown as dots in reagent solution 210) and particulate matter (shown as circles in reagent solution 210). As shown in FIGS. 2A-2D, as reagent solution 210 dries, the particulate matter inhibits the preferential deposition of reagent components at sides 208 of the sample chamber. As shown in FIG. 2D, the result is a dry reagent-particulate matter composition disposed on the substrate (e.g., a working electrode surface) in the sample chamber region, the composition having substantially uniform distribution of the detection reagent(s) attributable to the particulate matter being present in the reagent solution during the drying. FIG. 2E shows a top view of the portion of the sensor shown in FIG. 2D.

For ease of illustration, the area of the sample chamber consumed by the particulate matter in FIG. 2 is substantial. It will be appreciated that the particle density of the reagent solution/suspension may be adjusted to achieve a desired amount/configuration of particles in the sample chamber upon drying of the solution/suspension. For example, the particle density may be chosen to achieve uniform distribution of the analyte detection reagent, and also to provide less than a single layer of particles on the surface of the substrate. In other aspects, the particle density may be chosen to achieve uniform distribution of the analyte detection reagent, and also to provide a monolayer, bilayer, or more layers of the particles on the surface of the substrate.

Accordingly, in certain embodiments, the present disclosure provides sensors for determining the concentration of an analyte (e.g., glucose, a ketone, etc.) in a sample fluid. The sensors include a first substrate having a proximal end and a distal end, the first substrate defining a first side edge and a second side edge of the sensor extending from the proximal end to the distal end of the first substrate, the distal end being configured and arranged for insertion into a sensor reader. According to this aspect, the sensors also include a second substrate disposed over the first substrate, a working electrode disposed on one of the first and second substrates, a counter electrode disposed on one of the first and second substrates, and a spacer disposed between the first and second substrates and defining a sample chamber that comprises the working electrode and the counter electrode. Also according to this aspect, the sensors include a dry composition disposed on an area of the working electrode, the composition comprising an analyte detection reagent and conductive particles configured and arranged to provide for substantially uniform distribution of the detection reagent on the area of the working electrode.

By "substantially uniform distribution" of the detection reagent is meant that if the area of the working electrode upon which the dry composition is disposed was subdivided into equal sized smaller areas (or "sub-areas"), these sub-areas would each have the same or substantially the same quantity of disposed analyte detection reagent, within the uncertainty of the measurement method used to quantify the disposed reagent. In certain embodiments, the quantity of analyte detection reagent disposed on the sub-areas does not differ between sub-areas by more than about 25%. For example, the quantity of detection reagent disposed on the sub-areas does not differ between sub-areas by more than about 20%, 15%, 10%, 5%, 2%, or more than about 1%.

For example, a rectangular working electrode (with, e.g., a deposited enzyme and an osmium-based mediator) of width 1.5 mm and length 4 mm, could be carefully scribed into 3 smaller rectangular sub-areas, each 0.5 mm by 4 mm. Each sub-area could then be washed with buffer to extract the deposited enzyme and mediator into a known volume of liquid, e.g., about 1 mL. Enzyme activity assays could then be used to quantify the amount of enzyme in each sub-area, and/or atomic absorption spectroscopy (e.g., for osmium) could be used to quantify the amount of mediator.

The area of the working electrode on which the composition is disposed may comprise any desired amount of conductive particles. In certain aspects, the area of the working electrode on which the dry composition is disposed includes between about $10^2$ and $10^{10}$ conductive particles/mm$^2$. For example, the area of the working electrode may include between about $10^3$ and $10^9$ conductive particles/mm$^2$, between about $10^4$ and $10^8$ conductive particles/mm$^2$, between about $10^4$ and $10^7$ conductive particles/mm$^2$, or between about $10^5$ and $10^6$ conductive particles/mm$^2$. The particle density may depend, e.g., on the diameter of the particles, the concentration of the particles in the "wet" composition applied to the working electrode surface prior to drying, and/or the like.

According to certain embodiments, the sensors having substantially uniform distribution of the detection reagent on the area of the working electrode are in vitro analyte sensors. For example, the sensors may be in vitro analyte test strips. Such analyte sensors may have any desired configuration. For example, the sensors may be "tip fill" sensors, where the sample fluid is contacted at an aperture positioned at the proximal tip of the sensor for introducing the sample fluid into the sample chamber of the sensor. Alternatively, the sensors may be "side fill" sensors, where the sample fluid is contacted at an aperture positioned at a side edge of the sensor for introducing the sample fluid into the sample chamber of the sensor. Moreover, the sensors may have any desired electrode configuration. For example, the sensors may have the working and counter electrode on separate substrates and in a facing configuration. Alternatively, the sensors may have the working and counter electrodes disposed on a single substrate in a coplanar configuration.

Figure 4:
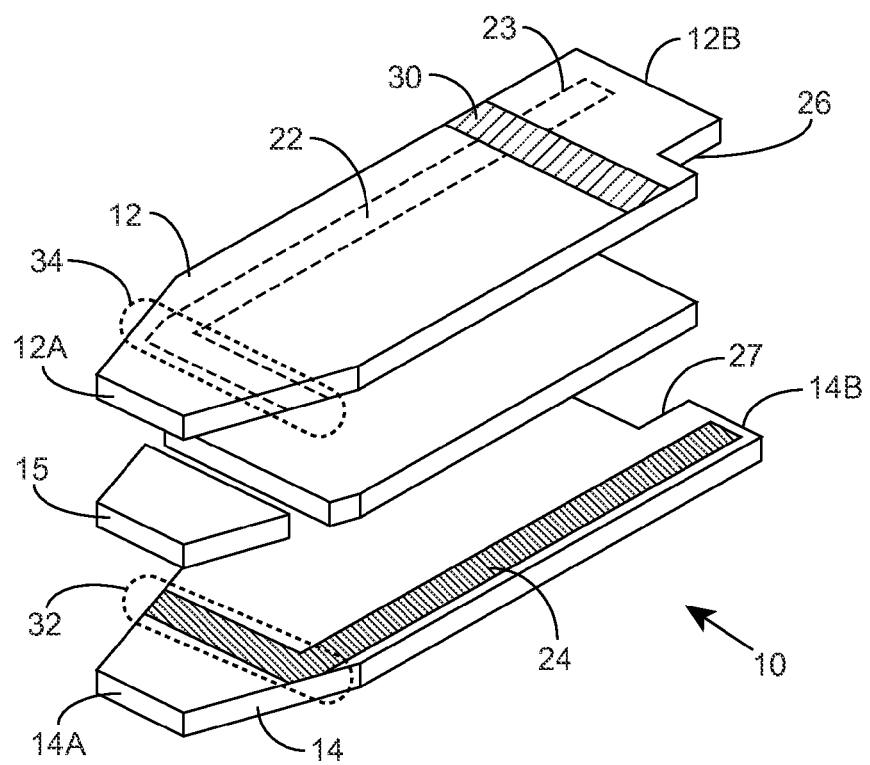
FIG. 4 is an exploded view of the sensor strip shown in FIG. 3, the layers illustrated individually with the electrodes in a first configuration.

Referring to the Drawings in general and FIG. 3 and FIG. 4 in particular, a first embodiment of a sensor 10 is schematically illustrated, herein shown in the shape of a strip. It is to be understood that the sensor may be any suitable shape. Sensor strip 10 has a first substrate 12, a second substrate 14, and a spacer 15 positioned therebetween. Sensor strip 10 includes at least one working electrode 24 and at least one counter electrode 22. Sensor strip 10 also includes an optional insertion monitor 30.

Sensor strip 10 has a first, proximal end 10A and an opposite, distal end 10B. At proximal end 10A, sample to be analyzed is applied to sensor 10. Proximal end 10A could be referred as 'the fill end', 'sample receiving end', or similar. Distal end 10B of sensor 10 is configured for operable, and usually releasable, connecting to a device such as a meter.

Sensor strip 10 is a layered construction, in certain embodiments having a generally rectangular shape, i.e., its length is longer than its width, although other shapes are possible as well, as noted above. The length of sensor strip 10 is from end 10A to end 10B.

The dimensions of a sensor may vary. In certain embodiments, the overall length of sensor strip 10 may be no less than about 10 mm and no greater than about 50 mm. For example, the length may be between about 30 and 45 mm; e.g., about 30 to 40 mm. It is understood, however that shorter and longer sensor strips 10 could be made. In certain embodiments, the overall width of sensor strip 10 may be no less than about 3 mm and no greater than about 15 mm. For example, the width may be between about 4 and 10 mm, about 5 to 8 mm, or about 5 to 6 mm. In one particular example, sensor strip 10 has a length of about 32 mm and a width of about 6 mm. In another particular example, sensor strip 10 has a length of about 40 mm and a width of about 5 mm. In yet another particular example, sensor strip 10 has a length of about 34 mm and a width of about 5 mm.

As provided above, sensor strip 10 has first and second substrates 12, 14, non-conducting, inert substrates which form the overall shape and size of sensor strip 10. Substrates 12, 14 may be substantially rigid or substantially flexible. In certain embodiments, substrates 12, 14 are flexible or deformable. Examples of suitable materials for substrates 12, 14 include, but are not limited to, polyester, polyethylene, polycarbonate, polypropylene, nylon, and other "plastics" or polymers. In certain embodiments the substrate material is "Melinex" polyester. Other non-conducting materials may also be used.

Substrate 12 includes first or proximal end 12A and second or distal end 12B, and substrate 14 includes first or proximal end 14A and second or distal end 14B.

As indicated above, positioned between substrate 12 and substrate 14 may be spacer 15 to separate first substrate 12 from second substrate 14. In some embodiments, spacer 15 extends from end 10A to end 10B of sensor strip 10, or extends short of one or both ends. Spacer 15 is an inert non-conducting substrate, typically at least as flexible and deformable (or as rigid) as substrates 12, 14. In certain embodiments, spacer 15 is an adhesive layer or double-sided adhesive tape or film that is continuous and contiguous. Any adhesive selected for spacer 15 should be selected to not diffuse or release material which may interfere with accurate analyte measurement. In certain embodiments, the thickness of spacer 15 may be constant throughout, and may be at least about 0.01 mm (10 μm) and no greater than about 1 mm or about 0.5 mm. For example, the thickness may be between about 0.02 mm (20 μm) and about 0.2 mm (200 μm). In one certain embodiment, the thickness is about 0.05 mm (50 μm), and about 0.1 mm (100 μm) in another embodiment.

The sensor includes a sample chamber for receiving a volume of sample to be analyzed; in the embodiment illustrated, particularly in FIG. 3, sensor strip 10 includes sample chamber 20 having an inlet 21 for access to sample chamber 20. In the embodiment illustrated, sensor strip 10 is a side-fill sensor strip, having inlet 21 present on a side edge of strip 10. Tip-fill sensors, having an inlet at, for example, end 10A, are also within the scope of this disclosure, as well as corner and top filling sensors.

Sample chamber 20 is configured so that when a sample is provided in chamber 20, the sample is in electrolytic contact with both a working electrode and a counter electrode, which allows electrical current to flow between the electrodes to effect the electrolysis (electrooxidation or electroreduction) of the analyte.

Sample chamber 20 is defined by substrate 12, substrate 14 and spacer 15; in many embodiments, sample chamber 20 exists between substrate 12 and substrate 14 where spacer 15 is not present. Typically, a portion of spacer 15 is removed to provide a volume between substrates 12, 14 without spacer 15; this volume of removed spacer is sample chamber 20. For embodiments that include spacer 15 between substrates 12, 14, the thickness of sample chamber 20 is generally the thickness of spacer 15.

Sample chamber 20 has a volume sufficient to receive a sample of biological fluid therein. In some embodiments, such as when sensor strip 10 is a small volume sensor, sample chamber 20 has a volume that is typically no more than about 1 μL, for example no more than about 0.5 μL, and also for example, no more than about 0.25 μL. A volume of no more than about 0.1 μL is also suitable for sample chamber 20, as are volumes of no more than about 0.05 μL and about 0.03 μL.

As provided above, the thickness of sample chamber 20 corresponds typically to the thickness of spacer 15. Particularly for facing electrode configurations, as in the sensor illustrated in FIG. 4, this thickness is small to promote rapid electrolysis of the analyte, as more of the sample will be in contact with the electrode surface for a given sample volume. In addition, a thin sample chamber 20 helps to reduce errors from diffusion of analyte into the sample chamber during the analyte assay, because diffusion time is long relative to the measurement time, which may be about 5 seconds or less.

As provided above, the sensor includes a working electrode and at least one counter electrode. The counter electrode may be a counter/reference electrode. If multiple counter electrodes are present, one of the counter electrodes will be a counter electrode and one or more may be reference electrodes.

The sensor includes at least one working electrode positioned within the sample chamber. In FIG. 4, working electrode 24 is illustrated on substrate 14. In alternate embodiments, a working electrode is present on a different surface or substrate, such as substrate 12. Working electrode 24 extends from the sample chamber 20, proximate first end 10A, to the other end of the sensor 10, end 10B, as an electrode extension called a "trace". The trace provides a contact pad 25 for providing electrical connection to a meter or other device to allow for data and measurement collection, as will be described later. Contact pad 25 may be positioned on a tab 27 that extends from the substrate on which working electrode 24 is positioned, such as substrate 12 or 14. In some embodiments, a tab has more than one contact pad positioned thereon. In alternate embodiments, a single contact pad is used to provide a connection to one or more electrodes; that is, multiple electrodes are coupled together and are connected via one contact pad.

As provided above, at least a portion of working electrode 24 is provided in sample chamber 20 for the analysis of analyte, in conjunction with the counter electrode.

Referring to FIG. 4 and in accordance with the present disclosure, a dry composition including at least one analyte detection reagent (e.g., an analyte-responsive enzyme and/or a redox mediator) and particulate matter (e.g., conductive particles, such as carbon nanopowder, conductive microspheres, and/or the like) may be disposed on a surface of an area of working electrode 24, e.g., all or a portion of the surface of working electrode region 32. The dry composition may be disposed on working electrode 24 prior to disposing spacer 15 on substrate 14. Alternatively, spacer 15 is first disposed on substrate 14 (creating a channel having working electrode 24 as its base, similar to the channel shown in FIG. 2), followed by application of an aqueous composition that includes at least one detection reagent and particulate matter to all or a portion of the surface of working electrode region 32. In accordance with the present disclosure, as the aqueous composition dries, the detection reagent(s) remain distributed substantially uniformly over the working electrode surface due to the presence of the particulate matter in the composition (see, e.g., FIG. 2).

For sensor 10, at least one counter electrode is positioned on one of first substrate 12 and second substrate 14 in the sample chamber. In FIG. 4, counter electrode 22 is illustrated on substrate 12. Counter electrode 22 extends from the sample chamber 20, proximate end 10A, to the other end of the sensor 10, end 10B, as an electrode extension called a "trace". The trace provides a contact pad 23 for providing electrical connection to a meter or other device to allow for data and measurement collection, as will be described later. Contact pad 23 may be positioned on a tab 26 that extends from the substrate on which counter electrode 22 is positioned, such as substrate 12. In some embodiments, a tab has more than one contact pad positioned thereon. In alternate embodiments, a single contact pad is used to provide a connection to one or more electrodes; that is, multiple electrodes are coupled together and are connected via one contact pad.

Referring to FIG. 4 and in accordance with the present disclosure, a polymer layer may be disposed on a surface of an area of counter electrode 22, e.g., all or a portion of the surface of counter electrode region 34. Exemplary polymer materials and layers thereof are described elsewhere herein. The polymer layer may serve as a physical solid barrier to prevent conductive particles disposed on the surface of the working electrode from forming a short connection between coplanar or facing working and counter electrodes of the sensor. In certain aspects, the polymer layer, upon wetting by a fluid sample (e.g., a blood sample of a subject), is able to conduct ions with a conductivity high enough to not limit the current of the sensor, and also maintains its physical integrity when wetted by the fluid sample to prevent any shorting throughout the entire analyte measurement period.

Working electrode 24 and counter electrode 22 may be disposed opposite to and facing each other to form facing electrodes. See for example, FIG. 4, which has working electrode 24 on substrate 14 and counter electrode 22 on substrate 12, forming facing electrodes. In this configuration, the sample chamber is typically present between the two electrodes 22, 24. Working electrode 24 and counter electrode 22 may alternately be positioned generally planar to one another, such as on the same substrate, to form coplanar or planar electrodes.

In some instances, it is desirable to be able to determine when the sample chamber of the sensor is sufficiently filled with sample. Sensor strip 10 may be indicated as filled, or substantially filled, by observing a signal between an optional indicator electrode and one or both of working electrode 24 or counter electrode 22 as sample chamber 20 fills with fluid. When fluid reaches the indicator electrode, the signal from that electrode will change. Suitable signals for observing include, for example, voltage, current, resistance, impedance, or capacitance between the indicator electrode and, for example, working electrode 24. Alternatively, the sensor may be observed after filling to determine if a value of the signal (e.g., voltage, current, resistance, impedance, or capacitance) has been reached indicating that the sample chamber is filled.

The optional indicator electrode may also be used to improve the precision of the analyte measurements. The indicator electrode may operate as a working electrode or as a counter electrode or counter/reference electrode. Measurements from the indicator electrode/working electrode may be combined (e.g., added or averaged) with those from the first counter/reference electrode/working electrode to obtain more accurate measurements.

The sensor or equipment that the sensor connected is with (e.g., a meter) may include a signal (e.g., a visual sign or auditory tone) that is activated in response to activation of the indicator electrode to alert the user that the sample chamber is beginning to fill with sample and/or that the sample chamber is sufficiently filled with sample to measure the analyte concentration. The sensor or equipment may be configured to initiate a reading when the indicator electrode indicates that the sample chamber has been filled with or without alerting the user. The reading may be initiated, for example, by applying a potential between the working electrode and the counter electrode and beginning to monitor the signals generated at the working electrode.

Figure 5:
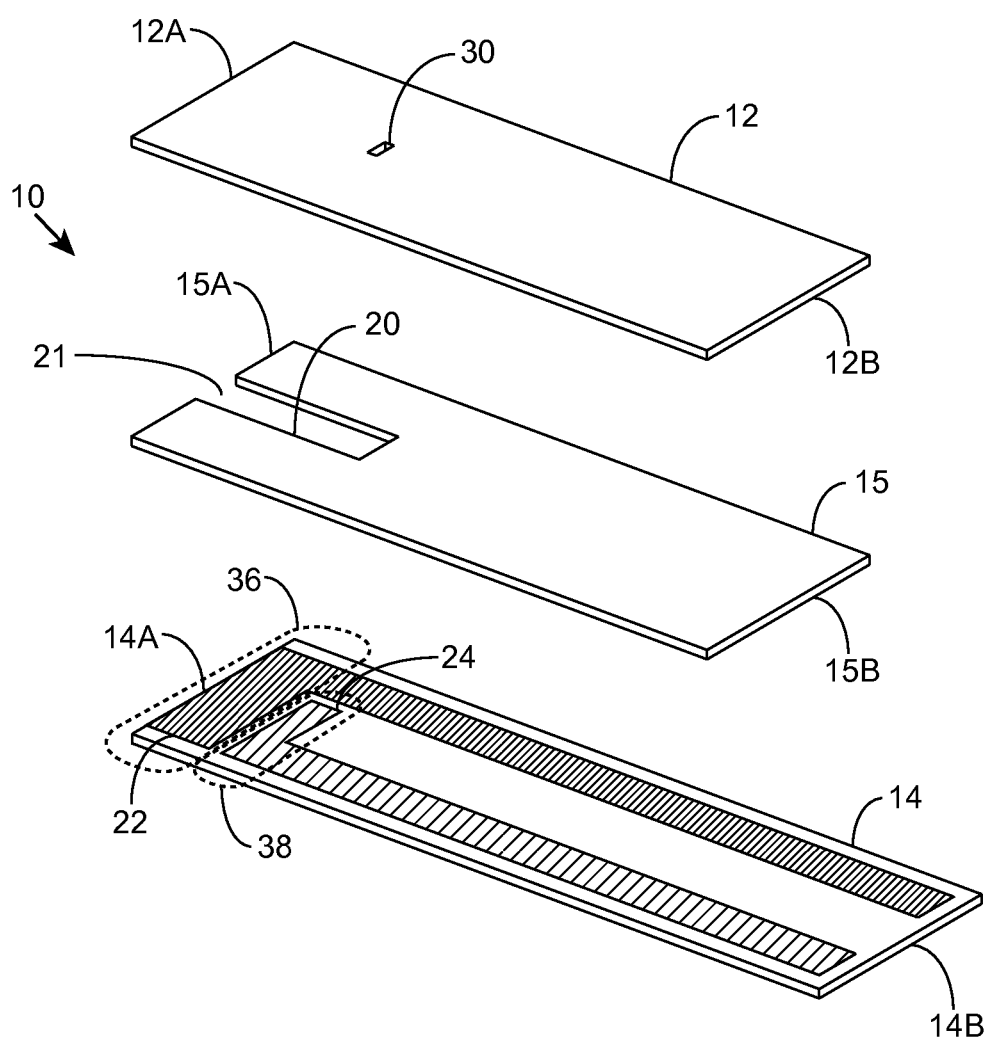
FIG. 5 is an exploded view of a second embodiment of a sensor strip in accordance with the present disclosure, the layers illustrated individually with the electrodes in a second configuration.

Referring to FIG. 5, an embodiment of an analyte sensor is illustrated as analyte sensor 10. The analyte sensor strip 10 has a first substrate 12, a second substrate 14, and a spacer 15 positioned therebetween. Analyte sensor strip 10 includes at least one working electrode 22 and at least one counter electrode 24.

Analyte sensor strip 10 has a first, proximal end and an opposite, distal end. At proximal end, sample to be analyzed is applied to sensor 10. Proximal end could be referred as "the fill end" or "sample receiving end". Distal end of sensor 10 is configured for operable connection to a device such as a meter. Sensor strip 10 is a layered construction, in certain embodiments having a generally rectangular shape, which is formed by first and second substrates 12, 14. Substrate 12 includes first or proximal end 12A and second or distal end 12B, and substrate 14 includes first or proximal end 14A and second or distal end 14B.

Sensor strip 10 includes sample chamber 20 having an inlet 21 for access to sample chamber 20. Sensor strip 10 is a tip-fill sensor, having inlet 21 at the proximal end. Sample chamber 20 is defined by substrate 12, substrate 14 and spacer 15. Generally opposite to inlet 21, through substrate 12 is a vent 30 from sample chamber 20.

For sensor 10, at least one working electrode 22 is illustrated on substrate 14. Working electrode 22 extends from end 14A into sample chamber 20 to end 14B. Sensor 10 also includes at least one counter electrode 24, in this embodiment on substrate 14. Counter electrode 24 extends from sample chamber 20, proximate first proximal end to distal end. Working electrode 22 and counter electrode 24 are present on the same substrate e.g., as planar or co-planar electrodes.

Referring to FIG. 5 and in accordance with the present disclosure, a dry composition including at least one analyte detection reagent (e.g., an analyte-responsive enzyme and/or a redox mediator) and particulate matter (e.g., conductive particles, such as carbon nanopowder, conductive microspheres, and/or the like) may be disposed on a surface of an area of working electrode 22, e.g., all or a portion of the surface of working electrode area 36. The dry composition may be disposed on working electrode 22 prior to disposing spacer 15 on substrate 14. Alternatively, spacer 15 is first disposed on substrate 14 (creating a channel having working electrode 22 as a portion of its base, similar to the channel shown in FIG. 2), followed by application of an aqueous composition that includes at least one detection reagent and particulate matter to an exposed portion of the surface of working electrode area 32. In accordance with the present disclosure, as the aqueous composition dries, the at least one detection reagent remains distributed substantially uniformly over the working electrode surface to which the composition is applied, due to the presence of the particulate matter in the composition (see, e.g., the principle schematically illustrated in FIG. 2).

Also referring to FIG. 5 and in accordance with the present disclosure, a polymer layer may be disposed on a surface of an area of counter electrode 24, e.g., all or a portion of the surface of counter electrode area 38. Exemplary polymer materials and layers thereof are described elsewhere herein. The polymer layer may serve as a physical solid barrier to prevent conductive particles disposed on or in the vicinity of the surface of the working electrode from forming a short connection between the working and counter electrodes of the sensor. In certain aspects, the polymer layer, upon wetting by a fluid sample (e.g., a blood sample of a subject), is able to conduct ions with a conductivity high enough to not limit the current of the sensor, and also maintains its physical integrity when wetted by the fluid sample to prevent any shorting throughout the entire analyte measurement period.

Sensors Having a Working Electrode with Increased Effective Surface Area

Embodiments of the present disclosure relate to sensors having a working electrode with increased effective surface area by disposition of conductive particulate matter (e.g., conductive microspheres) on a surface of the working electrode of the sensor, such as in vitro or in vivo analyte sensors. Also provided are methods of manufacturing the analyte sensors and methods of using the analyte sensors in analyte monitoring.

The inventors of the present disclosure have found that disposing one or more layers of conductive particles (e.g., conductive microspheres) on a surface of a working electrode increases the effective surface area of the working electrode. As a result of the increased effective surface area of the working electrode, higher peak currents, shorter test times, and/or more linear results may be obtained during operation of the sensor.

A working electrode surface having conductive microspheres disposed thereon is schematically illustrated in FIG. 6. FIG. 6A shows working electrode surface 604 having a monolayer of conductive microspheres disposed thereon. The microspheres are in contact with the working electrode surface, as well as with each other, such that each sphere acts as an extension of the electrode surface. In other aspects, provided are sensors having a working electrode surface with more than one layer of conductive microspheres disposed thereon. An example of a working electrode surface having more than one layer of conductive microspheres is schematically illustrated in FIG. 6B, where approximately two layers (i.e., a bilayer) of conductive microspheres are disposed on the working electrode. In this aspect, conductive microspheres of a first layer makes contact with the working electrode surface, with each other, and also with conductive microspheres of a second layer. The conductive microspheres of the second layer make contact with the conductive microspheres of the first layer, as well as each other. Whether one, two or more layers of conductive microspheres are provided on the surface of the working electrode, the result is that all or a majority of the spheres act as an extension of the working electrode surface, thereby increasing the effective surface area of the working electrode.

According to certain embodiments, one or more layers of conductive particles are disposed on a surface of the working electrode (e.g., by depositing a conductive particle-containing suspension on the working electrode surface, followed by drying), and an analyte detection solution that includes one or more analyte detection reagents (e.g., an analyte-responsive enzyme and/or a redox mediator) is deposited over the conductive particles. In other aspects, one or more layers of conductive particles are disposed on the surface of the working electrode by applying a conductive particle suspension that also includes one or more analyte detection reagents (e.g., an analyte-responsive enzyme and/or a redox mediator).

The desired number of layers of conductive particles on the working electrode surface may be achieved using any suitable approach. For example, when a particle-containing suspension is deposited on a working electrode surface, the particle density of the suspension may be controlled to achieve a monolayer, bilayer, trilayer, or more layers of conductive particles on the surface. Whether or not a particular particle density achieves the desired number of layers may be determined, e.g., via microscopic imaging of the particles disposed on the electrode surface. In certain aspects, the desired number of layers of conductive particles is achieved by first determining the particle density of a particle suspension required to achieve a monolayer of particles on the electrode surface (for particles having a particular diameter), and then increasing the particle density by a factor of two, three or more to achieve a bilayer, trilayer, or more layers, respectively, of conductive particles on the surface.

Other approaches for achieving the desired number of particle layers on the working electrode surface include inkjet deposition and spray deposition, both of which can be performed in multiple passes, such that the preceding pass is allowed to dry before a subsequent pass/layer is applied.

The conductive particles may be deposited over the entire surface of the working electrode. Alternatively, the surface of the working electrode on which the conductive particles are deposited is substantially limited to all or a portion of the working electrode surface positioned within the sample chamber of the sensor. For example, referring to the sensor embodiments shown in FIG. 4 and FIG. 5, the one or more layers of conductive particles may be disposed on the working electrode region substantially or entirely limited to working electrode regions 32 and 36, respectively, or a sub-region thereof.

Sensors Having Reduced Interference from Sample Fluid Components

Embodiments of the present disclosure relate to sensors having particulate matter (e.g., carbon nanopowder, microspheres, and/or the like) in a sample chamber of the sensor, such as in vitro or in vivo analyte sensors, such that the particulate matter excludes components that interfere with analyte measurement from entering the sample chamber. Also provided are methods of manufacturing the analyte sensors and methods of using the analyte sensors in analyte monitoring.

According to one aspect, sensors are provided that include a sufficient amount of particulate matter in the sample chamber such that the sample chamber is substantially filled with the particulate matter and, as a result, the entry into the sample chamber of interfering substances in a sample fluid is decreased or prevented during operation of the sensor. With reference to FIG. 4 and FIG. 5, the particulate matter (e.g., conductive microspheres) may be disposed in—and substantially fill—the sample chamber region formed by overlaying the spacer on the substrate that includes the working electrode, such that upon overlaying the top substrate onto the spacer, the particles substantially fill the resulting sample chamber. A number of variations are possible. For example, provided are sensors where a central or terminal portion of the sample chamber may be substantially devoid of particles, and the majority (or all) of the particles are disposed at the portion of the sample chamber proximal to the sample entry port/aperture.

The volume of the sample chamber occupied by the particulate matter (e.g., conductive particles, such as conductive microspheres) may be determined during the sensor manufacturing process, e.g., by depositing a suspension of particulate matter (optionally with detection reagents) in which the concentration of the particulate matter in the suspension determines the volume of the sample chamber occupied by the particulate matter. The particulate matter may, for example, occupy from about 10% to about 90% of the volume of the sample chamber, e.g., from about 25% to about 90%, from about 50% to about 90%, from about 75% to about 90%, or from about 80% to about 90% of the volume of the sample chamber. In certain aspects, the volume of the sample chamber occupied by the particulate matter is greater than about 90%, e.g., greater than about 95%.

Any particulate matter suitable for decreasing or preventing entry of an undesired interfering substance may be used. For example, based on the size of the interfering substance, particles having a diameter within a particular range may be chosen such that—when the particles are disposed in the sample chamber—the spaces between the particles are sufficiently small such that entry of the interfering substance into the sample chamber is prevented. According to one embodiment, the sample fluid is blood and red blood cells (or "erythrocytes") constitute the undesired interfering substance. The dimensions of red blood cells of various population of interest (e.g., humans) are known in the art. For example, the diameter of human red blood cells ranges from 6-8 µm. Accordingly, when it is desired to decrease or prevent entry of human red blood cells into the sample chamber, the diameter of the particles may be chosen so that the maximum dimension of the spaces (or "voids") between the particles is less than or equal to about 6-8 µm. Generally, the particle size should be chosen such that entry of the undesired interfering substance into the sample chamber is sufficiently decreased or prevented, but that the particles are not so small that the flow rate of a fluid sample into the sample chamber is markedly reduced as a result of the particles in the sample chamber excessively impeding the flow of the sample fluid. As such, the particles may be chosen according to the requirements and limitations of the particular sensor (and analyte monitoring system) to be used.

Exemplary features and components of the sensors provided by the present disclosure are described in greater detail below. It will be appreciated that any such features and components may be employed—or present in—any of the sensors described above, including sensors having improved uniformity of distribution of one or more analyte detection reagents, increased effective working electrode surface area, and/or reduced entry of interfering components into the sample chamber.

Working Electrode

As summarized previously herein, an analyte sensor includes a working electrode and a reference/counter electrode, comprising a first portion located in the sample chamber and a second portion for connection to a meter. The working electrode may be formed from a suitable conducting material. The conducting material may have relatively low electrical resistance and may be electrochemically inert over the potential range of the sensor during operation and substantially transparent. In certain aspects, the working electrode includes a material selected from the group consisting of gold, carbon, platinum, ruthenium, palladium, silver, silver chloride, silver bromide, and combinations thereof. The working electrode may be a thin layer of gold, tin oxide, platinum, ruthenium dioxide or palladium, indium tin oxide, zinc oxide, fluorine doped tin oxide, as well as other non-corroding materials known to those skilled in the art. The working electrode can be a combination of two or more conductive materials. For example, the working electrode may be constructed from thin layer of gold in the sample chamber and of carbon outside the sample chamber.

The working electrode can be applied on a substrate by any of a variety of methods, including by being deposited, such as by vapor deposition or vacuum deposition or otherwise sputtered, printed on a flat surface or in an embossed or otherwise recessed surface, transferred from a separate carrier or liner, etched, or molded. Suitable methods of printing include screen-printing, piezoelectric printing, ink jet printing, laser printing, photolithography, painting, gravure roll printing, transfer printing, and other known printing methods.

Particles

Any particulate matter suitable for improving the distribution of analyte detection reagents, increasing the effective surface area of a working electrode, and/or preventing interfering substances from entering a sample chamber, may be used in the sensors of the present disclosure.

In certain embodiments, the particles comprise nanomaterials (e.g., conductive nanomaterials). Exemplary nanomaterials include, but are not limited to, aluminum nanomaterial, carbon nanomaterial, cobalt carbon coated nanomaterial, copper nanomaterial, copper nanomaterial, copper-zinc alloy nanomaterial, diamond nanomaterial, gold nanomaterial, iron nanomaterial, iron-nickel alloy nanomaterial, molybdenum nanomaterial, magnesium nanomaterial, nickel nanomaterial, palladium nanomaterial, platinum nanomaterial, silver nanomaterial, silver-copper alloy nanomaterial, tantalum nanomaterial, tin nanomaterial, indium doped tin oxide nanomaterial, titanium nanomaterial, titanium nitride nanomaterial, tungsten nanomaterial, zinc nanomaterial, calcium oxide nanomaterial, hydroxyapatite nanomaterial, indium nanomaterial, silica nanomaterial, silicon nanomaterial, silicon dioxide nanomaterial, silicon nitride nanomaterial, silicon carbide nanomaterial, and the like. Exemplary nanomaterials may also include polymers such as polyethylene, polymethylene, polypropylene, or polystyrene, wherein the polymer is not covalently conjugated to components of the analyte sensor. Other exemplary nanomaterials are well known and commercially available from suppliers, such as, for example, Sigma-Aldrich.

When the particles comprise a nanomaterial, the nanomaterial may be a nanopowder or a nanoparticle, such as a carbon nanopowder. In such embodiments, the nanopowder or nanoparticle will have particles having a diameter of from about 1 nm to about 300 nm, including about 10 nm to about 290 nm, about 15 nm to about 275 nm, about 20 nm to about 250 nm, about 30 nm to about 225 nm, about 35 nm to about 200 nm, about 40 nm to about 175 nm, about 45 nm to about 150 nm, about 50 nm to about 125 nm, about 55 nm to about 100 nm, and about 60 nm to about 75 nm.

In certain aspects, the particles are nanospheres or microspheres. In certain aspects, the particles are conductive microspheres. The conductive microspheres may comprise a polymer core made of a polymer material selected from, but not limited to, polyethylene, polymethylene, polypropylene, polystyrene, and combinations thereof. The polymer core may be coated with one or more conductive layers. The conductive layer may include any suitable conducting material, including but not limited to, gold, carbon, platinum, ruthenium, palladium, silver, silver chloride, silver bromide, and combinations thereof.

According to certain embodiments, the microspheres are hollow or porous. The pores of porous microspheres, for example, provide additional surface area for disposing a conductive coating and/or one or more analyte detection reagents (e.g., an analyte-responsive enzyme and/or redox mediator) onto the surface of the microsphere. This additional surface area may improve the performance of the sensor by enhancing conductivity, providing greater access of the analyte to the detection reagents, and the like.

When the sensors include microspheres (e.g., conductive microspheres), the average diameter of the conductive microspheres may vary. For example, the conductive microspheres may have a diameter of from about 0.5 µm to about 100 µm, including about 1 µm to about 50 µm, about 2.5 µm to about 25 µm, and about 5 µm to about 10 µm. In certain aspects, sensors of the present disclosure include conductive microspheres having an average diameter of about 5 µm.

Counter Electrode

The counter electrode may be constructed in a manner similar to the working electrode. As used herein, the term "counter electrode" refers to an electrode that functions as a counter electrode, or both a reference electrode and a counter electrode. The counter electrode can be formed, for example, by depositing electrode material onto a substrate. The material of the counter electrode may be deposited by a variety of methods such as those described above for the working electrode. In certain aspects, the counter electrode includes a material selected from the group consisting of gold, carbon, platinum, ruthenium, palladium, silver, silver chloride, silver bromide, and combinations thereof. For example, suitable materials for the counter electrode include Ag/AgCl or Ag/AgBr printed on a non-conducting substrate. According to certain embodiments, the counter electrode comprises a thin conductive layer such as gold, tin oxide, indium tin oxide, layered with AgCl or AgBr, for example.

Polymer Layer

As described elsewhere herein, sensors of the present disclosure may include conductive particles in the sample chamber to improve the distribution of one or more detection reagents, increase the effective surface area of the working electrode, and/or inhibit entry of certain interfering substances into the sample chamber. However, if the conductive particles are misplaced outside the sample chamber region, if the particles are excessively stacked in the sample chamber region, or generally if the particles form a physical and/or electrical connection between the working and counter electrode, the particles can cause an electrical short between the working electrode and counter electrode during operation of the sensor, preventing the sensor from functioning properly.

The inventors of the present disclosure have discovered that disposing a polymer layer onto the counter electrode of a sensor having conductive microparticles reduces or eliminates electrical shorting between the working and counter electrodes. The polymer layer (or coating) serves as a physical solid barrier to prevent the loose conducting particles from forming a short connection between coplanar or facing working and counter electrodes of the sensor.

In certain aspects, the polymer layer, upon wetting by a fluid sample (e.g., a blood sample of a subject), is able to conduct ions with a conductivity high enough to not limit the current of the sensor, and also maintains its physical integrity when wetted by the fluid sample to prevent any shorting throughout the entire analyte measurement period. One approach to improve the physical integrity of the polymer is to cross-link the polymer using compatible cross-linkers.

According to one embodiment, the polymer layer is a copolymer, such as a copolymer of vinyl pyridine and styrene grafted with propyl sulfonate and polyethylene glycol (PEG) having the following formula:

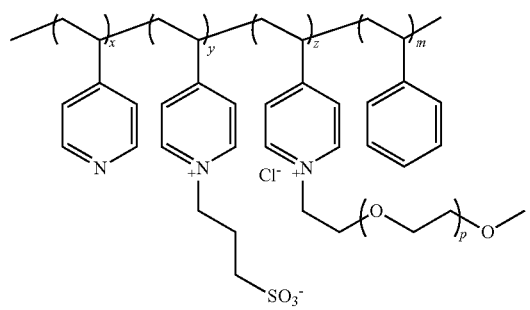

In the above polymer, the presence of the ionic moieties and PEG confers good ionic conductivity upon swelling with water. In addition, this polymer can be readily cross-linked with multi-epoxy functionalized cross-linkers to enhance its physical integrity when exposed to a fluid sample.

Any suitable polymer/copolymer, e.g., a polymer or copolymer having sufficient ion conductivity and/or adequate physical integrity under wet conditions, may be used. For example, the counter electrode may be coated with a polymer formed using a resin, such as an aliphatic urethane polymer, which is a polyurethane-based resin containing carboxyl functional groups.

Additional polymers that find use in the sensors described herein include, but are not limited to, those described in U.S. Pat. No. 6,932,894 and U.S. Patent Application Publication No. 2008/0179187, the disclosures of which are incorporated herein in their entireties for all purposes.

Electrode Configuration

A variety of analyte sensor electrode configurations are known in the art which may be suitable for use in the disclosed analyte sensors. For example, suitable configurations can include configurations having a working electrode positioned in opposition to a reference/counter electrode or configurations having the working electrode positioned coplanar with the reference/counter electrode. Additional suitable electrode configurations include, but are not limited to, those described in U.S. patent application Ser. No. 11/461,725, filed Aug. 1, 2006; U.S. patent application Ser. No. 12/102,374, filed Apr. 14, 2008; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. Patent Application Publication No. 2009/0095625; U.S. Pat. No. 6,616,819; U.S. Pat. No. 6,143,164; and U.S. Pat. No. 6,592,745; the disclosures of each of which are incorporated herein by reference in their entireties for all purposes.

Analytes

A variety of analytes can be detected and quantified using the analyte sensors disclosed herein including, but not limited to, glucose, blood β-ketone, ketone bodies, lactate, acetyl choline, amylase, bilirubin, cholesterol, chorionic gonadotropin, creatine kinase (e.g., CK-MB), creatine, DNA, fructosamine, glutamine, growth hormones, hormones, ketones, lactate, peroxide, prostate-specific antigen, prothrombin, RNA, thyroid stimulating hormone, and troponin, in sample of body fluid. Analyte sensors may also be configured to detect and/or quantify drugs, such as, for example, antibiotics (e.g., gentamicin, vancomycin, and the like), digitoxin, digoxin, drugs of abuse, theophylline, and warfarin. Assays suitable for determining the concentration of DNA and/or RNA are disclosed in U.S. Pat. No. 6,281, 006 and U.S. Pat. No. 6,638,716, the disclosures of each of which are incorporated by reference herein.

Analyte-Responsive Enzyme

The disclosed analyte sensors may include in the sample chamber an analyte-responsive enzyme which is capable of transferring electrons to or from a redox mediator and the analyte. For example, a glucose oxidase (GOD) or glucose dehydrogenase (GDH) can be used when the analyte is glucose. A lactate oxidase can be used when the analyte is lactate. These enzymes catalyze the electrolysis of an analyte by transferring electrons between the analyte and the electrode via the redox mediator. In one embodiment, the analyte-responsive enzyme is disposed on the working electrode. In certain embodiments, the analyte-responsive enzyme is immobilized on the working electrode. This is accomplished, for example, by cross linking the analyte-responsive enzyme with a redox mediator on the working electrode, thereby providing a sensing layer on the working electrode. In an alternative embodiment, the analyte-responsive enzyme is disposed adjacent to the electrode. Generally, the analyte-responsive enzyme and redox mediator are positioned in close proximity to the working electrode in order to provide for electrochemical communication between the analyte-responsive enzyme and redox mediator and the working electrode. Generally, the analyte-responsive enzyme and redox mediator are positioned relative to the reference/counter electrode such that electrochemical communication between the analyte-responsive enzyme and the redox mediator and the reference/counter electrode is minimized. Additional analyte-responsive enzymes and cofactors which may be used in connection with the disclosed analyte sensors are described in U.S. Pat. No. 6,736,957, the disclosure of which is incorporated by reference herein.

In some embodiments, in order to facilitate the electrochemical reaction of the analyte sensor the sample chamber also includes an enzyme co-factor. For example, where the analyte-responsive enzyme is glucose dehydrogenase (GDH), suitable cofactors include pyrroloquinoline quinone (PQQ), nicotinamide adenine dinucleotide NAD+ and flavin adenine dinucleotide (FAD).

In certain embodiments, the analyte detected and/or measured by the sensor described herein may be ketone and the enzyme included in the sensor is hydroxybutyrate dehydrogenase.

Redox Mediator

In addition to the analyte-responsive enzyme, the sample chamber may include a redox mediator. In one embodiment, the redox mediator is immobilized on the working electrode. Materials and methods for immobilizing a redox mediator on an electrode are provided in U.S. Pat. No. 6,592,745, the disclosure of which is incorporated by reference herein. In an alternative embodiment, the redox mediator is disposed adjacent to the working electrode.

The redox mediator mediates a current between the working electrode and the analyte when present. The mediator functions as an electron transfer agent between the electrode and the analyte.

Almost any organic or organometallic redox species can be used as a redox mediator. In general, suitable redox mediators are rapidly reducible and oxidizable molecules having redox potentials a few hundred millivolts above or below that of the standard calomel electrode (SCE), and typically not more reducing than about −200 mV and not more oxidizing than about +400 mV versus SCE. Examples of organic redox species are quinones and quinhydrones and species that in their oxidized state have quinoid structures, such as Nile blue and indophenol. Unfortunately, some quinones and partially oxidized quinhydrones react with functional groups of proteins such as the thiol groups of cysteine, the amine groups of lysine and arginine, and the phenolic groups of tyrosine which may render those redox species unsuitable for some of the sensors of the present invention, e.g., sensors that will be used to measure analyte in biological fluids such as blood.

In certain cases, mediators suitable for use in the analyte sensors have structures which prevent or substantially reduce the diffusional loss of redox species during the period of time that the sample is being analyzed. Suitable redox mediators include a redox species bound to a polymer which can in turn be immobilized on the working electrode. Useful redox mediators and methods for producing them are described in U.S. Pat. Nos. 5,262,035; 5,264,104; 5,320, 725; 5,356,786; 6,592,745; and 7,501,053, the disclosure of each of which is incorporated by reference herein. Any organic or organometallic redox species can be bound to a polymer and used as a redox mediator. In certain cases, the redox species is a transition metal compound or complex. The transition metal compounds or complexes may be osmium, ruthenium, iron, and cobalt compounds or complexes. In certain cases, the redox mediator may be an osmium compounds and complex.

One type of non-releasable polymeric redox mediator contains a redox species covalently bound in a polymeric composition. An example of this type of mediator is poly (vinylferrocene).

Alternatively, a suitable non-releasable redox mediator contains an ionically-bound redox species. Typically, these mediators include a charged polymer coupled to an oppositely charged redox species. Examples of this type of mediator include a negatively charged polymer such as Nafion® (Dupont) coupled to a positively charged redox species such as an osmium or ruthenium polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide.

In another embodiment, the suitable non-releasable redox mediators include a redox species coordinatively bound to the polymer. For example, the mediator may be formed by coordination of an osmium or cobalt 2,2'-bipyridyl complex to poly(1-vinyl imidazole) or poly(4-vinyl pyridine).

The redox mediator may be a osmium transition metal complex with one or more ligands having a nitrogen-containing heterocycle such as 2,2'-bipyridine, 1,10-phenanthroline or derivatives thereof. Furthermore, the redox mediator may also have one or more polymeric ligands having at least one nitrogen-containing heterocycle, such as pyridine, imidazole, or derivatives thereof. These mediators exchange electrons rapidly between each other and the electrodes so that the complex may be rapidly oxidized and reduced.

In particular, it has been determined that osmium cations complexed with two ligands containing 2,2'-bipyridine, 1,10-phenanthroline, or derivatives thereof, the two ligands not necessarily being the same, and further complexed with a polymer having pyridine or imidazole functional groups form particularly useful redox mediators in the small volume sensors. Derivatives of 2,2'-bipyridine for complexation with the osmium cation may be 4,4'-dimethyl-2,2'-bipyridine and mono-, di-, and polyalkoxy-2,2'-bipyridines, such as 4,4'-dimethoxy-2,2'-bipyridine, where the carbon to oxygen ratio of the alkoxy groups is sufficient to retain solubility of the transition metal complex in water. Preferred derivatives of 1,10-phenanthroline for complexation with the osmium cation are 4,7-dimethyl-1,10-phenanthroline and mono-,di-, and polyalkoxy-1,10-phenanthrolines, such as 4,7-dimethoxy-1,10-phenanthroline, where the carbon to oxygen ratio of the alkoxy groups is sufficient to retain solubility of the transition metal complex in water. Exemplary polymers for complexation with the osmium cation include poly(1-vinyl imidazole), e.g., PVI, and poly(4-vinyl pyridine), e.g., PVP, either alone or with a copolymer. Most preferred are redox mediators with osmium complexed with poly(1-vinyl imidazole) alone or with a copolymer.

Suitable redox mediators have a redox potential between about −150 mV to about +400 mV versus the standard calomel electrode (SCE). For example, the potential of the redox mediator can be between about −100 mV and +100 mV, e.g., between about −50 mV and +50 mV. In one embodiment, suitable redox mediators have osmium redox centers and a redox potential more negative than +100 mV versus SCE, e.g., the redox potential is more negative than +50 mV versus SCE, e.g., is near −50 mV versus SCE.

In one embodiment, the redox mediators of the disclosed analyte sensors are air-oxidizable. This means that the redox mediator is oxidized by air, e.g., so that at least 90% of the mediator is in an oxidized state prior to introduction of sample into the sensor. Air-oxidizable redox mediators include osmium cations complexed with two mono-, di-, or polyalkoxy-2,2'-bipyridine or mono-, di-, or polyalkoxy-1,10-phenanthroline ligands, the two ligands not necessarily being the same, and further complexed with polymers having pyridine and imidazole functional groups. In particular, $Os[4,4'\text{-dimethoxy-2,2'-bipyridine}]_2Cl^{+/+2}$ complexed with poly(4-vinyl pyridine) or poly(1-vinyl imidazole) attains approximately 90% or more oxidation in air.

In one specific embodiment, the redox mediator is 1,10 Phenanthrolene-5,6-dione (PQ).

To prevent electrochemical reactions from occurring on portions of the working electrode not coated by the mediator, a dielectric may be deposited on the electrode surrounding the region with the bound redox mediator. Suitable dielectric materials include waxes and non-conducting organic polymers such as polyethylene. Dielectric may also cover a portion of the redox mediator on the electrode. The covered portion of the mediator will not contact the sample, and, therefore, will not be a part of the electrode's working surface.

Although it can be advantageous to minimize the amount of redox mediator used, the range for the acceptable amount of redox mediator typically has a lower limit. The minimum amount of redox mediator that may be used is the concentration of redox mediator that is necessary to accomplish the assay within a desirable measurement time period, for example, no more than about 5 minutes, or no more than about 1 minute, or no more than about 30 seconds, or no more than about 10 seconds, or no more than about 5 seconds, or no more than about 3 seconds, or no more than about 1 second or less.

The analyte sensor can be configured (e.g., by selection of redox mediator, positioning of electrodes, etc.) such that the sensor signal is generated at the working electrode with a measurement period of no greater than about 5 minutes and such that a background signal that is generated by the redox mediator is no more than five times a signal generated by oxidation or reduction of 5 mM analyte. In some embodiments, the analyte sensor is configured such that the background signal that is generated by the redox mediator is less than the signal generated by oxidation or reduction of 5 mM glucose. In some embodiments, the background that is generated by the redox mediator is no more than 25% of the signal generated by oxidation or reduction of 5 mM analyte, e.g., no more than 20%, no more than 15% or no more than 5%. In certain embodiments, the analyte is glucose and the background that is generated by the redox mediator is no more than 25% of the signal generated by oxidation or reduction of 5 mM glucose, e.g., no more than 20%, no more than 15% or no more than 5% of the signal generated by electrolysis of glucose.

Sorbent Material

The sample chamber may be empty prior to entry of the sample. Optionally, the sample chamber can include a sorbent material to sorb and hold a fluid sample during detection and/or analysis. Suitable sorbent materials include polyester, nylon, cellulose, and cellulose derivatives such as nitrocellulose. The sorbent material facilitates the uptake of small volume samples by a wicking action which may complement or replace any capillary action of the sample chamber. In addition or alternatively, a portion or the entirety of the wall of the sample chamber may be covered by a surfactant, such as, for example, Zonyl FSO.

In some embodiments, the sorbent material is deposited using a liquid or slurry in which the sorbent material is dissolved or dispersed. The solvent or dispersant in the liquid or slurry may then be driven off by heating or evaporation processes. Suitable sorbent materials include, for example, cellulose or nylon powders dissolved or dispersed in a suitable solvent or dispersant, such as water. The particular solvent or dispersant should also be compatible with the material of the electrodes (e.g., the solvent or dispersant should not dissolve the electrodes).

One of the functions of the sorbent material is to reduce the volume of fluid needed to fill the sample chamber of the analyte sensor. The actual volume of sample within the sample chamber is partially determined by the amount of void space within the sorbent material. Typically, suitable sorbents consist of about 5% to about 50% void space. In one embodiment, the sorbent material consists of about 10% to about 25% void space.

Fill Assist

The analyte sensors can be configured for top-filling, tip-filling, corner-filling, and/or side-filling. In some embodiments, the analyte sensors include one or more optional fill assist structures, e.g., one or more notches, cut-outs, indentations, and/or protrusions, which facilitate the collection of the fluid sample. For example, the analyte sensor can be configured such that the proximal end of the analyte sensor is narrower than the distal end of the analyte sensor. In one such embodiment, the analyte sensor includes a tapered tip at the proximal end of the analyte sensor, e.g., the end of the analyte sensor that is opposite from the end that engages with a meter.

Additional fill assist structures are described in U.S. Patent Publication No. 2008/0267823, the disclosure of which is incorporated by reference herein; and U.S. patent application Ser. No. 11/461,725, filed Aug. 1, 2006, the disclosure of which is incorporated by reference herein.

Signal Enhancement

In certain cases, the analyte sensor comprising particulate matter (e.g., conductive particles) on a working electrode surface provides a signal (e.g., a peak current) from electrolysis of an analyte in a sample that is at least 5%, or 10%, or 15%, or 20%, or 30%, or 40%, or 50%, or 60%, or 70%, or 80%, or 90%, or 100%, or 120%, or 130% higher than the signal generated from electrolysis of the analyte in the sample using a similar analyte sensor but not comprising particulate matter (e.g., conductive particles) on a working electrode surface. In certain embodiments, the higher signal is generated within 0.01 second, or 0.03 second, or 0.01 second, or 0.3 second, or 0.6 second, or 1 second, or 1.3 seconds, or 1.6 seconds, or 2 seconds, or 3 seconds, or 4 seconds, or 5 seconds, or more of applying the sample to the analyte sensor.

As used herein, "signal" refers to current, charge, resistance, voltage, impedance, or log or integrated values thereof that is related to the concentration of the analyte being analyzed by the sensor.

Accuracy

In certain embodiments of the present disclosure, inclusion of particulate matter (e.g., conductive particles) on a working electrode surface results in an increase in the accuracy of the analyte measurements from the sensor. For example, inclusion of particulate matter (e.g., conductive particles) on a working electrode surface may result in better correlation between the analyte concentration as determined by an in vitro analyte monitoring device (e.g., based on signals detected from the in vitro analyte sensor by a device operably connected to the sensor, for example, a meter) and a reference analyte concentration. In certain instances, inclusion of particulate matter (e.g., conductive particles) on a working electrode surface results in analyte concentrations as determined by the signals detected from the analyte sensor that are within 50% of a reference value, such as within 40% of the reference value, including within 30% of the reference value, or within 20% of the reference value, or within 10% of the reference value, or within 5% of the reference value, or within 2% of the reference value, or within 1% of the reference value. In some cases, 75% of the analyte sensors as described herein demonstrate the accuracy (e.g., is within a percentage of a reference value, as described above). In some cases, 80% or more, or 90% or more, including 95% or more, or 97% or more, or 99% or more of the analyte sensors as described herein demonstrate the accuracy (e.g., is within a percentage of a reference value, as described above).

As an alternative measure of accuracy, in some cases, inclusion of particulate matter (e.g., conductive particles) on a working electrode surface results in analyte concentrations as determined by the signals detected from the analyte sensor that are within Zone A of the Clarke Error Grid Analysis. For example, inclusion of particulate matter (e.g., conductive particles) on a working electrode surface may result in analyte concentrations as determined by the signals detected from the analyte sensor that are within Zone A of the Clarke Error Grid Analysis for 75% or more of the analyte sensors, such as 80% or more, or 90% or more, including 95% or more, or 97% or more, or 99% or more of the analyte sensors. In certain instances, inclusion of conductive particles in the sample chamber results in analyte concentrations as determined by the signals detected from the analyte sensor that are within Zone A or Zone B of the Clarke Error Grid Analysis. For example, inclusion of conductive particles in the sample chamber may result in analyte concentrations as determined by the signals detected from the analyte sensor that are within Zone A or Zone B of the Clarke Error Grid Analysis for 75% or more of the analyte sensors, such as 80% or more, or 90% or more, including 95% or more, or 97% or more, or 99% or more of the analyte sensors. Further information regarding the Clarke Error Grid Analysis is found in Clarke, W. L. et al. "Evaluating Clinical Accuracy of Systems for Self-Monitoring of Blood Glucose" *Diabetes Care*, vol. 10, no. 5, 1987: 622-628.

Methods of Determining Analyte Concentration

The sensors described herein find use in methods for determining the concentration of an analyte in a fluid sample from a subject. Generally, these methods include contacting a fluid sample with the sensor, generating a sensor signal at the working electrode, and determining the concentration of the analyte using the sensor signal. It will be understood that the subject methods may employ any of the sensors described herein, e.g., sensors having improved uniformity of distribution of one or more analyte detection reagents, increased effective working electrode surface area, and/or reduced entry of interfering components into the sample chamber.

A variety of approaches may be employed to determine the concentration of the analyte. In certain aspects, an electrochemical analyte concentration determining approach is used. For example, determining the concentration of the analyte using the sensor signal may be performed by coulometric, amperometric, potentiometric, or any other convenient electrochemical detection technique.

According to certain embodiments, the subject methods include obtaining the sample from a subject. When the sample is a blood sample, the sample may be obtained, e.g., using a lancet to create an opening in a skin surface at which blood subsequently presents. The blood sample may be obtained from the finger of a subject. Alternatively, the blood sample may be obtained from a region of the subject having a lower nerve end density as compared to a finger. Obtaining a blood sample from a region having a lower nerve end density as compared to a finger is generally a less painful approach for obtaining a blood sample and may improve patient compliance, e.g., in the case of a diabetes patient where regular monitoring of blood glucose levels is critical for disease management.

Methods of Making Analyte Sensors

Also provided by the present disclosure are methods of manufacturing analyte sensors. In certain aspects, methods are provided that include forming a working electrode on a first substrate, forming a spacer layer on the first substrate, the spacer layer defining a sample chamber region on the first substrate, and applying a reagent composition on a surface of the working electrode in the sample chamber region. The reagent composition may include one or more analyte detection reagents (e.g., an analyte-responsive enzyme and/or a redox mediator) and particulate matter (e.g., conductive microspheres), where the particulate matter provides for even distribution of the detection reagent(s) as the reagent composition dries on the working electrode.

The sample chamber region on the first substrate includes at least a portion of a working electrode surface. Generally, the reagent composition is applied to all or a portion of the working electrode surface in the sample chamber region, thereby generating a modified working electrode surface in the sample chamber region on which one or more analyte detection reagents are substantially uniformly distributed.

Optionally, the methods further comprise disposing a counter electrode on the first substrate (e.g., on region of the first substrate distinct from the region on which the working electrode is disposed), or alternatively, disposing a counter electrode on a second substrate to be overlayed on the first substrate (thereby generating a facing electrode pair). Manufacturing the sensor is generally completed by overlaying a second substrate on the spacer layer and singulating individual sensors (e.g., by dye cutting, etc.) from the starting substrate material. General approaches for manufacturing analyte sensors are known in the art and are described, e.g., in U.S. Pat. No. 7,866,026, the full disclosure of which is incorporated herein by reference in its entirety for all purposes.

The present disclosure also provides methods of manufacturing analyte sensors, which methods include forming a working electrode on a first substrate, and disposing one or more layers of conductive material (e.g., conductive microspheres) on the working electrode, where the one or more layers make up an ordered array of conductive microspheres. By using conductive material (e.g., conductive microspheres) having a consistent size and shape, the conductive material is capable of being stacked into ordered arrays, with easily tailored surface area and void volume. For example, the number of layers of conductive microspheres may be selected to provide a desired effective surface area of the working electrode (e.g., where the effective surface area can be increased or decreased by increasing or decreasing the number of layers of conductive microspheres, respectively). Alternatively, or additionally, the size distribution of the conductive microspheres may be selected to provide a desired void volume within the array of conductive microspheres.

Also provided are methods of manufacturing analyte sensors, which methods include forming a working electrode on a first substrate, and disposing one or more layers of conductive microspheres on the working electrode, where a number of layers of the one or more layers of conductive microspheres is selected to provide a desired effective surface area of the working electrode. Optionally, the one or more layers make up an ordered array of conductive microspheres. The size distribution of the conductive microspheres may be selected to provide a desired void volume within the one or more layers of conductive microspheres.

In addition, the present disclosure provides of manufacturing analyte sensors, which methods include forming a working electrode on a first substrate, and disposing one or more layers of conductive microspheres on the working electrode, where a size distribution of the conductive microspheres is selected to provide a desired void volume within the one or more layers of conductive microspheres. The number of layers of the one or more layers of conductive microspheres may be selected to provide a desired effective surface area of the working electrode. The one or more layers optionally make up an ordered array of conductive microspheres.

Utility

The subject sensors and methods find use in a variety of different applications where, e.g., the accurate determination of an analyte concentration by an analyte sensor is desired. For example, the methods are useful for obtaining and accurately determining the concentration of one or more analytes in a bodily sample, e.g., a blood sample.

The following examples are offered by way of illustration and not by way of limitation.

EXPERIMENTAL

Example 1

Figure 7:
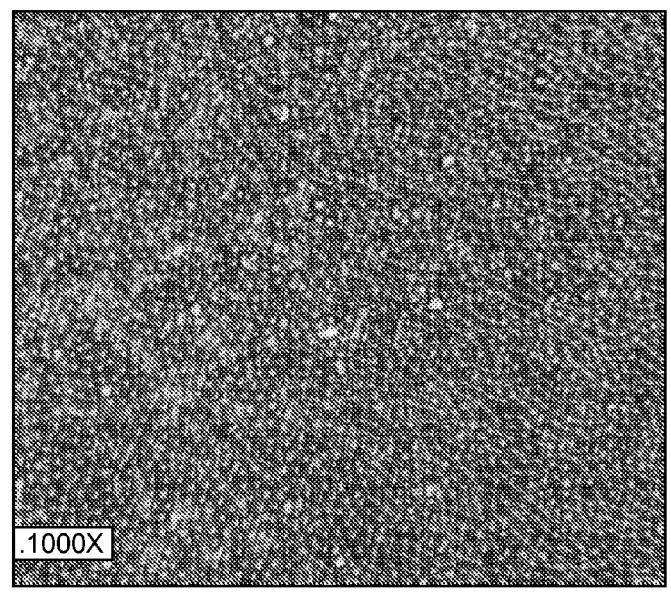
FIG. 7 is a graph showing the peak currents and response times of analyte sensors having no conductive particles or various numbers of layers of conductive particles in their sample chambers.

Sensors with Conductive Microspheres to Maximize Reagent Distribution and Electrode Surface Area In the present example, microspheres having poly(styrene) cores with a diameter of 4.99 microns (44% of total mass) were used. The poly(styrene) cores were coated with 0.062 microns Ni (24% of total mass), followed by 0.039 microns Au (32% of total mass). Particle density was approximately 2.5 g/mL. A 2.5% (w/v) tenuous microsphere suspension was prepared in a 0.1% (w/v) Triton X-100 aqueous solution. The suspension was then deposited by pipette onto Au-coated polyester film working electrodes with a series of coverages varying from 1 to 2 monolayers of Au microspheres. FIG. 7 provides an example photograph showing an approximately one monolayer of microspheres deposited, as there are minimal voids and the hexagonal close packing pattern is clearly visible in many spots.

Figure 8:
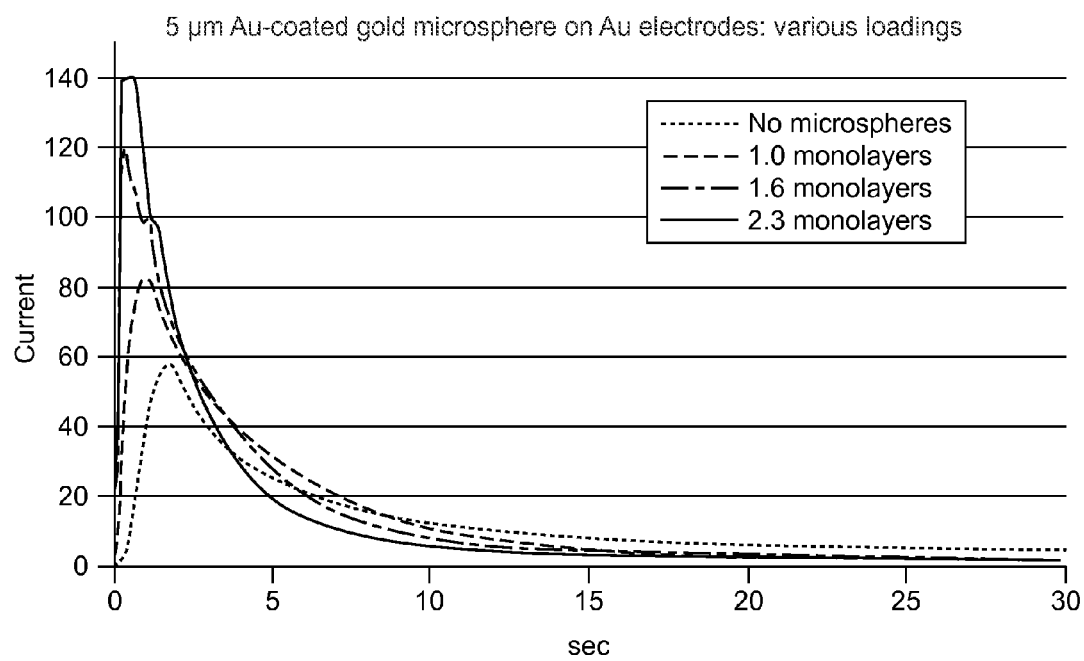
FIG. 8 is a graph showing the average currents (n=1 to 3) for different Au-coated microsphere loadings.

Next, a reagent solution including FAD-dependent glucose dehydrogenase (FAD-GDH; 4 units per sensor) and an osmium complex-based redox mediator (1.5 μg per strip) was deposited over the microspheres, and the microsphere-coated strip halves were paired with Ag/AgCl-coated counter electrode strip halves. The Ag/AgCl was first coated with a aliphatic urethane polymer to eliminate any short circuits that could be caused by misplaced microspheres. The assembled strips, along with control strips not containing Au-coated microspheres, were then tested with high control solution. FIG. 8 is a graph showing the average currents (n=1 to 3) for different Au-coated microsphere loadings.

As shown in FIG. 8, the peak current increases as the Au-coated microsphere loading increases. At the same time, the response time (i.e., the time for the current to decrease to one half of its peak value) decreases. Accordingly, the microspheres achieve the desired effect.

Example 2

Sensors with Polymer on Ag/AgCl Counter Electrode and Carbon Nanopowder on Carbon Working Electrode In this example, the following polymer was disposed on an Ag/AgCl counter electrode of a sensor having carbon nanopowder disposed on the working electrode to improve uniformity of reagent distribution and increase the effective surface area of the working electrode:

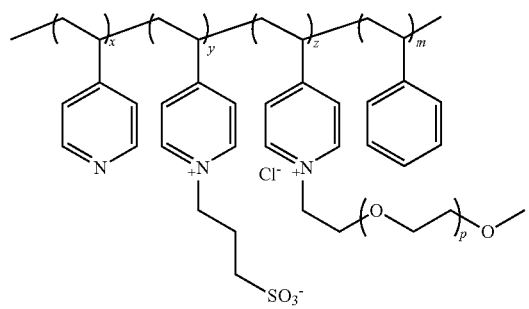

First, two stock solutions were prepared: (a) 50 mg/ml of the above polymer in 55%/45% ethanol/water with 1 mg/mL Igepal CO-610, 5 mg/mL Pluronic F-108, 1 mg/mL NaCl and 25 mM HEPES buffer and (b) 200 mg/ml poly(ethylene glycol) diglycidyl ether (Mw=400) in a mixture of 80% ethanol and 20% 10 mM hepes buffer (pH 8.0).

The final coating solution was prepared by mixing solutions (a) and (b) in a 20:1 ratio and rocking the solution for 30 minutes. A substrate including an Ag/AgCl counter electrode solution was then coated with the final coating solution at a deposition rate of 2.4 μL/cm, followed by drying at 80° C. under air. A clear thin film was formed on top of the counter electrode trace. Checking with a multimeter probe indicated that the film insulated the underlying Ag/AgCl counter electrode. A control Ag/AgCl counter electrode was coated with 2 mg/mL Igepal CO-610, 10 mg/mL Pluronic F-108, 2 mg/mL NaCl and 50 mM HEPES buffer in 90%/10% water/ethanol.

Carbon nanopowder was used as the conducting particle on a carbon working electrode included on a second substrate. A solution containing 2.5% carbon nanopowder and other standard working electrode detection reagents (FAD-GDH enzyme (4 Unit per strip), osmium transition metal mediator (1.5 μg per strip)) was coated in the working electrode channel. These substrates were then paired with the substrates including the counter electrode with and without the polymer coating, as described above. The combined substrates were cut to make electrochemical test strips.

Shorting between the working and counter electrodes was checked by applying a 100 mV voltage over the two sides of a strip on a potentiostat without applying any glucose solution to the strip channel. A current indicated the presence of shorting. The results showed that the strips without the polymer coating had about a 50% shorting rate, while the strips with the polymer coating disposed on the counter electrode did not exhibit any shorting.

The glucose current profiles of the non-shorted strips from the group of strips without the polymer coating and the strips from the polymer coated group were compared when a glucose solution was applied. It was found that strips from the two groups gave indistinguishable glucose current profiles, indicating that the polymer coating indeed provided the necessary ionic conductivity.

Example 3

Sensors with Polymer on Ag/AgCl Counter Electrode and Carbon Nanopowder on Gold Working Electrode In this example, the same polymer coating was disposed on a counter electrode to perform the same experiment as described in Example 2. Here, however, gold-coated polyester, rather than carbon, was used as the working electrode. The results showed that the polymer coating prevented shorting from occurring between the working and counter electrodes.

Example 4

Sensors with Neorez R-9603 Polymer on Ag/AgCl Counter Electrode and Gold-Coated Polystyrene Microspheres on Gold Working Electrode In this experiment, the conductive particles on the working electrode side were gold-coated polystyrene microspheres (5 μm diameters). The polymer coating was formed using NEOREZ® R-9603 aliphatic urethane polymer (DSM NeoResins, Waalwijk, The Netherlands). The experimental details were as described above in Example 1. The larger size of the gold-coated microspheres used in this study was more likely to cause shorting between the working and counter electrodes. However, such shorting did not occur in the strips that included the polymer coating on the counter electrode, indicating the effectiveness of the polymer coating in preventing shorting between the working and counter electrodes in the presence of larger conductive particles, e.g., 5 μm diameter conductive microspheres. In addition, the strips successfully delivered very high peak current (140 μA), indicating sufficient ionic conductivity of the polymer coating.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A sensor for determining the concentration of an analyte in a sample fluid, the sensor comprising:
    a first substrate having a proximal end and a distal end, the first substrate defining a first side edge and a second side edge of the sensor extending from the proximal end to the distal end of the first substrate, the distal end being configured and arranged for insertion into a sensor reader;
    a second substrate disposed over the first substrate;
    a working electrode disposed on one of the first and second substrates;
    a counter electrode disposed on one of the first and second substrates;
    a spacer disposed between the first and second substrates and defining a sample chamber that comprises the working electrode and the counter electrode; and
    a dry composition disposed on an area of the working electrode, the composition comprising an analyte detection reagent and electrically conductive particles, wherein the analyte detection reagent comprises an analyte-responsive enzyme and a redox mediator, wherein the analyte-responsive enzyme and the redox mediator are uniformly distributed on the area of the working electrode, wherein the electrically conductive particles provide for the uniform distribution of the analyte-responsive enzyme and the redox mediator on the area of the working electrode, wherein the conductive particles comprise nanoparticles or microspheres, wherein the dry composition is not disposed on the counter electrode.

2. The sensor of claim 1, wherein the area of the working electrode on which the composition is disposed comprises between about $10^4$ and $10^7$ conductive particles/mm$^2$.

3. The sensor of claim 1, wherein the conductive particles comprise a carbon nanopowder.

4. The sensor of claim 1, wherein the conductive particles are microspheres.

5. The sensor of claim 4, wherein the microspheres comprise a polymer coated with a conducting material.

6. The sensor of claim 5, wherein the microspheres are gold-coated polystyrene microspheres.

7. The sensor of claim 4, wherein the microspheres have a diameter of 0.5 µm to about 100 µm.

8. The sensor of claim 1, wherein the sensor comprises a polymer layer disposed on the counter electrode.

9. The sensor of claim 8, wherein the polymer layer is configured to prevent the conductive particles disposed on the working electrode from forming an electrical connection between the working electrode and the counter electrode.

10. The sensor of claim 8, wherein the polymer layer comprises a copolymer of vinyl pyridine and styrene.

11. The sensor of claim 10, wherein the vinyl pyridine and styrene are grafted with propyl sulfonate and polyethylene glycol.

12. The sensor of claim 8, wherein the polymer layer comprises a polyurethane-based resin.

13. The sensor of claim 12, wherein the polyurethane-based resin comprises carboxyl functional groups.

14. The sensor of claim 1, wherein the working electrode and counter electrode independently comprise a material selected from the group consisting of: gold, carbon, platinum, ruthenium, palladium, silver, silver chloride, silver bromide, and combinations thereof.

15. The sensor of claim 1, wherein the counter electrode comprises Ag/AgCl.

16. The sensor of claim 1, wherein the working electrode is disposed on the first substrate and the counter electrode is disposed on the second substrate.

17. The sensor of claim 1, wherein the working electrode and the counter electrode are disposed on the same substrate.

18. The sensor of claim 1, wherein the analyte is glucose or a ketone body.

19. The sensor of claim 18, wherein the analyte is glucose, and wherein the analyte-responsive enzyme is glucose dehydrogenase or glucose oxidase.

20. The sensor of claim 1, wherein the redox mediator comprises a transition metal complex.

21. The sensor of claim 20, wherein the transition metal complex comprises a transition metal selected from the group consisting of osmium, ruthenium, iron and cobalt.

22. The sensor of claim 21, wherein the transition metal is osmium.

23. The sensor of claim 20, wherein the transition metal complex comprises two or more ligands coordinately bound to a transition metal, wherein at least one of the ligands is a heterocyclic nitrogen-containing bidentate ligand.

24. The sensor of claim 23, wherein the transition metal is osmium.

25. The sensor of claim 1, wherein the sample chamber is sized to contain a volume of no more than about 1 µL of sample fluid.

26. The sensor of claim 1, wherein the sample chamber is sized to contain a volume of no more than about 0.5 µL of sample fluid.

27. The sensor of claim 1, wherein the conductive particles comprise nanoparticles.

28. The sensor of claim 27, wherein the nanoparticles have a diameter of 35 nm to 200 nm.

* * * * *